(12) United States Patent
Frigstad et al.

(10) Patent No.: US 9,517,159 B2
(45) Date of Patent: Dec. 13, 2016

(54) OCCLUSION IMPLANT

(71) Applicant: Conceptus, Inc., Mountain View, CA (US)

(72) Inventors: John R. Frigstad, St. Anthony, MN (US); William S. Tremulis, Minnetrista, MN (US); James R. Mujwid, Crystal, MN (US); Betsy Swann, Grass Valley, CA (US)

(73) Assignee: Bayer HealthCare LLC, Whippany, NJ (US)

( * ) Notice: Subject to any disclaimer, the term of this patent is extended or adjusted under 35 U.S.C. 154(b) by 0 days.

(21) Appl. No.: 13/742,279

(22) Filed: Jan. 15, 2013

(65) Prior Publication Data

US 2013/0186409 A1    Jul. 25, 2013

Related U.S. Application Data

(62) Division of application No. 12/616,726, filed on Nov. 11, 2009, now Pat. No. 8,356,600.

(60) Provisional application No. 61/113,456, filed on Nov. 11, 2008.

(51) Int. Cl.
*A61F 6/22* (2006.01)

(52) U.S. Cl.
CPC ....... *A61F 6/225* (2013.01); *A61F 6/22* (2013.01)

(58) Field of Classification Search
CPC ............... A61F 6/00; A61F 6/06; A61F 6/14; A61F 6/142; A61F 6/144; A61F 6/146; A61F 6/148; A61F 6/16; A61F 6/20; A61F 6/202; A61F 6/22; A61F 6/225;A61B 17/12022; A61B 17/12168; A61B 17/12172; A61B 17/12177; A61B 17/12181; A61B 17/12027; A61B 17/12031
USPC  128/830–833, 836, 838–840, 843; 623/1.11, 1.12, 1.17, 1.18, 1.2; 606/108, 606/191–193; 604/104–107
See application file for complete search history.

(56) References Cited

U.S. PATENT DOCUMENTS

| | | |
|---|---|---|
| 4,509,504 A | 4/1985 | Brundin |
| 4,834,091 A | 5/1989 | Ott |
| 5,968,053 A | 10/1999 | Revelas |
| 6,096,052 A | 8/2000 | Callister et al. |
| 6,432,116 B1 | 8/2002 | Callister et al. |
| 6,447,530 B1 | 9/2002 | Ostrovsky et al. |
| 6,736,822 B2 | 5/2004 | McClellan et al. |
| 6,896,682 B1 | 5/2005 | McClellan et al. |
| 7,073,504 B2 | 7/2006 | Callister et al. |
| 7,406,969 B2 | 8/2008 | Duchon et al. |
| 7,621,276 B2 | 11/2009 | Tal et al. |
| 2001/0041900 A1 | 11/2001 | Callister et al. |
| 2005/0045183 A1 | 3/2005 | Callister et al. |
| 2005/0081862 A1 | 4/2005 | Callister et al. |
| 2005/0085844 A1* | 4/2005 | Tremulis et al. ............. 606/193 |

(Continued)

*Primary Examiner* — Victoria J Hicks
*Assistant Examiner* — Raymond E Harris
(74) *Attorney, Agent, or Firm* — Aseem Mehta (57) ABSTRACT

Contraceptive and/or sterilization methods and devices are disclosed which may improve the speed of tubal occlusion and mechanisms for anchoring for a contraceptive device. In accordance with some embodiments, improvements may be made to the delivery catheter to induce trauma and create faster tubal occlusion, improvements may be made to the occlusion device to prevent migration and induce trauma, and improvements may be made to the occlusion device to reduce the total volume of in-growth required compared to conventional expansive occlusion devices.

8 Claims, 13 Drawing Sheets

(56) References Cited

U.S. PATENT DOCUMENTS

| | | | |
|---|---|---|---|
| 2005/0192616 A1* | 9/2005 | Callister et al. | 606/193 |
| 2005/0209633 A1* | 9/2005 | Callister et al. | 606/200 |
| 2006/0009798 A1* | 1/2006 | Callister et al. | 606/200 |
| 2006/0116709 A1* | 6/2006 | Sepetka et al. | 606/200 |
| 2007/0227544 A1* | 10/2007 | Swann et al. | 128/831 |
| 2007/0244439 A1 | 10/2007 | Mujwid et al. | |
| 2008/0135054 A1 | 6/2008 | Callister et al. | |
| 2008/0154256 A1 | 6/2008 | Payne et al. | |
| 2009/0084386 A1 | 4/2009 | McClellan et al. | |
| 2010/0163054 A1 | 7/2010 | Breznel et al. | |

* cited by examiner

OCCLUSION IMPLANT

RELATED APPLICATIONS

This application is a divisional of co-pending U.S. patent application Ser. No. 12/616,726 filed on Nov. 11, 2009, and also claims the benefit of U.S. Provisional Application No. 61/113,456, filed Nov. 11, 2008.

BACKGROUND

Embodiments of the present invention relate to the field of permanent tubal occlusion. More specifically, embodiments are directed to a device and method for placement of an occlusion device into a fallopian tube to achieve permanent occlusion. Conventional contraceptive strategies generally fall within three categories: physical barriers, drugs and surgery. While each have certain advantages, they also suffer from various drawbacks. Barriers such as condoms and diaphragms are subject to failure due to breakage, displacement and misuse. Drug strategies which rely on artificially controlling hormone levels suffer from known and unknown side-effects from prolonged use. Finally, surgical procedures, such as tubal ligation and vasectomy, involve the costs and attendant risks of surgery and are frequently not reversible.

In response to the aforementioned difficulties and inefficiencies of conventional contraceptive strategies, a number of implantable and permanent sterilization products have been developed to physically block the passage of reproductive cells between the ovary and uterus. Generally, these implantable permanent sterilization products are positioned within the fallopian tube so as to promote tissue in-growth, and over time, they physically occlude the fallopian tube.

While such implantable sterilization products are effective and minimally invasive, still further improvements would be desirable. For instance, it would be desirable to provide an occlusion device that reduces the requisite in-growth area to create the desired fallopian tube blockage. It would be desirable to provide an occlusion device having improved structures and/or mechanisms for anchoring the device. Further, it would be desirable to provide a system to provide enhanced trauma inducement within the musculature layer of the fallopian tube to increase the level of fibro-proliferative tissue response that ultimately enables tissue in-growth. Some or all of these advantages are provided by the devices and methods described hereinbelow.

SUMMARY

Embodiments of the present invention generally provide improved contraceptive and/or sterilization methods and devices. Embodiments generally improve the speed of tubal occlusion and mechanisms for anchoring for a contraceptive device.

In one embodiment of the present invention, the occlusion device is at least in part expandable within a body lumen from a first configuration suitable for insertion into the chosen location within the body lumen, to a second configuration larger than the first configuration to facilitate fastening of the occlusion device to the wall of the body lumen and creating an obstruction to block the body lumen.

In accordance with some embodiments, improvements may be made to the delivery catheter to induce trauma and create faster tubal occlusion. The delivery catheter may have an elongated shaft having a distal end portion and a lumen extending therein with an occlusion device restrained within the lumen. A surface of the distal end portion of the elongated shaft may include a plurality of shark skin oriented textures. The textures allow for smooth entry of the elongated shaft into a body lumen such as a fallopian tube, whereas retraction of the elongated shaft of out of the fallopian tube causes trauma to the fallopian tube which may promote the healing response and tissue in-growth into the deposited occlusion device.

The delivery catheter may include an elongated shaft which is equipped with features which can be expanded from and retracted back into the elongated shaft. For example, the elongated shaft may have a distal end portion and a lumen extending therein. A slit is provided in the distal end portion of the elongated shaft, with a wire that is expandable through and retractable into the slit. The wires may be expanded out of the elongated shaft prior to or during delivery of the occlusion device to induce trauma to the fallopian tube, and retracted into the elongated shaft prior to removing the catheter from the fallopian tube to avoid trauma to the ostium.

In accordance with some embodiments, improvements may be made to the occlusion device to prevent migration and induce trauma. The occlusion device may have a tubular frame member including protruding features attached the frame in a helical arrangement to resist displacement by the natural peristaltic pumping forces within a fallopian tube. The occlusion device may have an open framework comprising triangular or diamond-like shapes having closed ends that face outward proximally, distally and radially from the occlusion device to create engagement anchors in a starburst-like configuration. The occlusion device may comprise a series of linked ovals which, when deployed are folded within a middle portion of the device and not folded at the proximal and distal end portions of the device.

The occlusion device may include a proximal portion, a distal portion, and a traverse member connecting the proximal portion and the distal portion, a first plurality of arms outwardly expandable from the proximal portion of the occlusion device, and a second plurality of arms outwardly expandable from the distal portion of the occlusion device such that the first plurality of arms and second plurality of arms are expandable in opposition directions and overlap when expanded. The traverse frame member may be contractible or rigid.

In accordance with some embodiments, improvements may be made to the occlusion device to reduce the total volume of in-growth required compared to conventional expansive occlusion devices. The occlusion device may include a tubular frame member and a rod disposed within and running through the center of the tubular frame member, with the rod filling at least half of the cross-sectional area of the tubular frame member when in the expanded configuration. The occlusion device may have an open walled frame, where the frame can be constrained within a catheter in a rolled up configuration and deliverable within a fallopian tube in a substantially flat configuration.

BRIEF DESCRIPTION OF THE DRAWINGS

FIG. 6-FIG. 10A illustrate side views of occlusion devices in accordance with embodiments of the present invention.

FIG. 14A-FIG. 17B illustrate side views of occlusion devices in accordance with embodiments of the present invention.

DETAILED DESCRIPTION

Embodiments of the present invention generally provide improved contraceptive and/or sterilization methods and devices. More specifically, some embodiments provide an occlusion device and method which can be used to inhibit pregnancy, typically for the long-term inhibition of pregnancy, and often providing permanent contraception or sterilization.

Various embodiments and aspects will be described with reference to details discussed below and the accompanying drawings will illustrate the various embodiments. The following description and drawings are illustrative of the invention and are not to be construed as limiting the invention. Numerous specific details are described to provide a thorough understanding of various embodiments of the present invention. However, in certain instances, well-known or conventional details are not described in order to provide a concise discussion of embodiments of the present invention.

Figure 1:
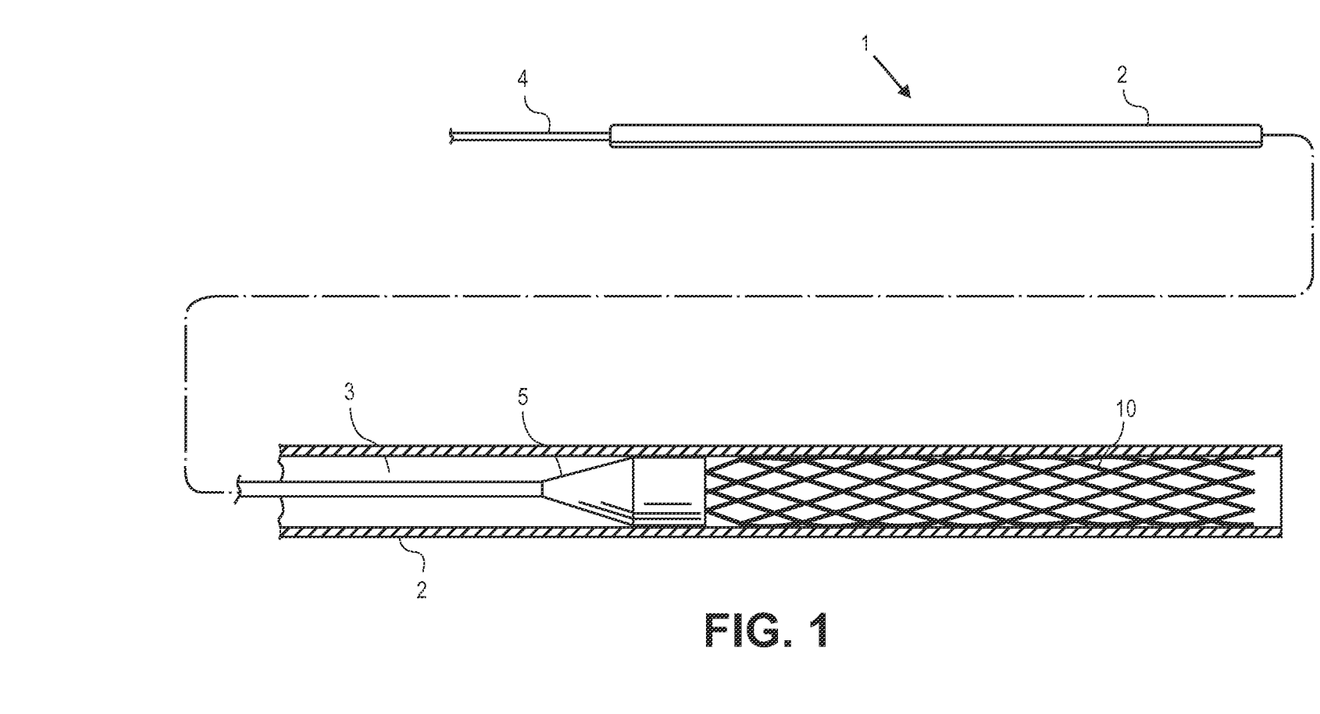
FIG. 1 illustrates a delivery catheter in accordance with an embodiment of the present invention.

FIG. 1 is an illustration of a delivery catheter 1 useful in the delivery of an occlusion device 10 in accordance with embodiments of the present invention. Delivery catheter 1 generally comprises an elongated shaft 2 having a lumen 3 extending therein. The occlusion device 10 may be self expanding. For example, occlusion device 10 may be deformed into a smaller configuration when within the lumen 3 of the delivery catheter, and expanded into a larger configuration within a body lumen by longitudinally displacing the occlusion device 10 out of the distal end of the delivery catheter. A pusher 4 with an enlarged head 5 slidably received within the lumen 3 of the delivery catheter can be used to longitudinally displace the occlusion device 10 out of the distal end of the delivery catheter.

Over-the-wire (OTW) designs or techniques may additionally be utilized to deliver occlusion devices in accordance with embodiments of the present invention. Placement of the occlusion device may be made directly or with the use of another device, for example a hysteroscope or other type of laparascope. Those skilled in the art will recognize that various combinations, modifications and alternative embodiments may be equivalents and may be included in the invention without departing from the scope of the invention as set forth herein. For example, other acceptable variations of the delivery devices and the occlusion devices are disclosed in patent application Ser. No. 08/770,123, filed on Dec. 18, 1996, now U.S. Pat. No. 7,037,504; Ser. No. 09/112,085, filed Jul. 8, 1998, now U.S. Pat. No. 6,906,052; Ser. No. 09/468,749, filed on Dec. 21, 1999, now U.S. Pat. No. 6,432,116; Ser. No. 11/048,237, filed Feb. 1, 2005; Ser. No. 10/746,131, filed Dec. 24, 2003; Ser. No. 10/972,857, filed Oct. 25, 2004; Ser. No. 10/880,355, filed Jun. 28, 2004; Ser. No. 09/911,551, filed Jul. 23, 2001; Ser. No. 12/035,219, filed Feb. 21, 2008; Ser. No. 11/695,887, filed Apr. 3, 2007; Ser. No. 11/048,221, filed Jan. 31, 2005; and Prov. No. 61/113,456 filed Nov. 11, 2008 the complete contents of which are incorporated as if set forth in full herein.

Figure 2:
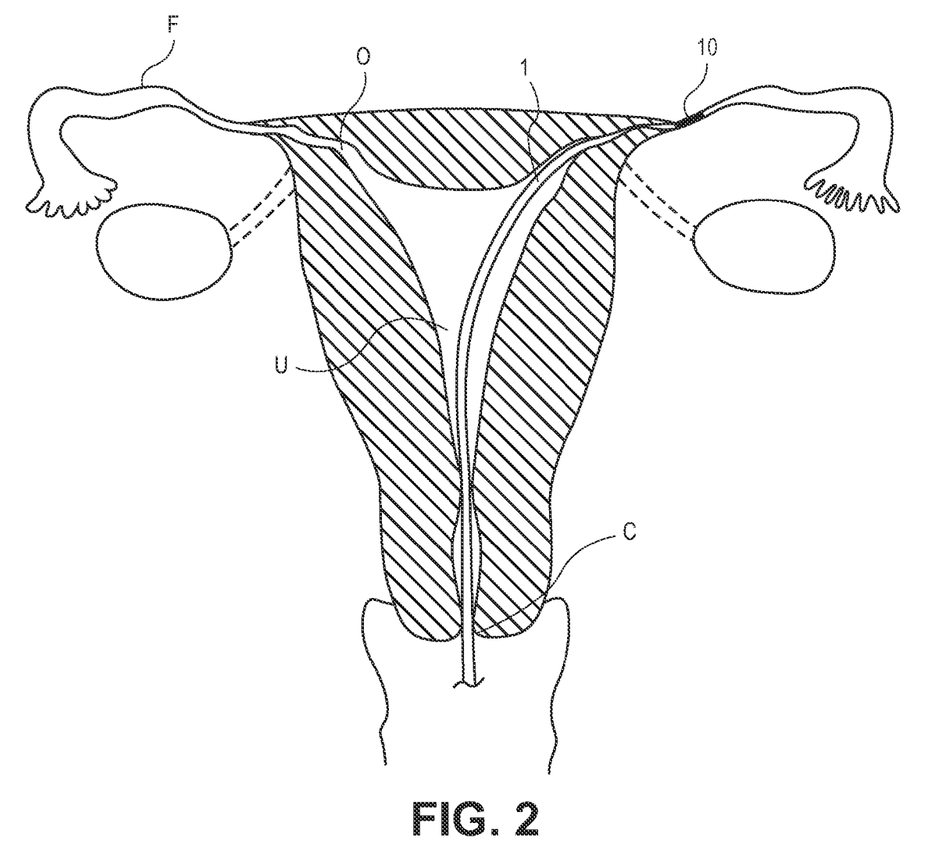
FIG. 2 illustrates the female anatomy for deployment of the contraceptive devices in accordance with embodiments of the present invention.
Figure 3:
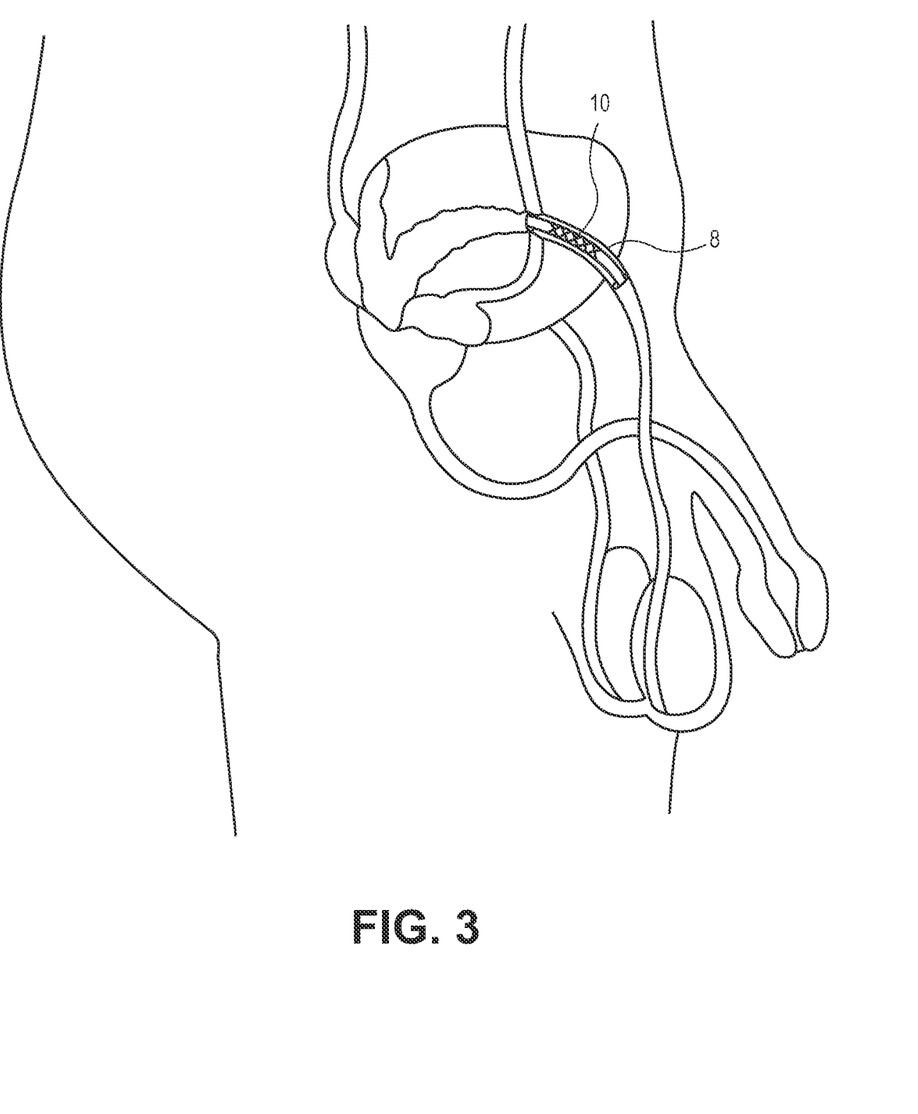
FIG. 3 illustrates the male anatomy deployment of the contraceptive devices in accordance with embodiments of the present invention.

FIG. 2 is an illustration of an occlusion device 10 implanted into a fallopian tube F of a female patient. A delivery catheter 1 can be inserted through cervix C, into the uterus U, and guided into a fallopian tube F through a tubal ostium O. Once the precise location within the fallopian tube is reached, the occlusion device 10 is released. Occlusion device 10 may also be inserted into other body lumens such as the vas deferens 8 of the male reproductive anatomy, as illustrated in FIG. 3.

Figure 4:
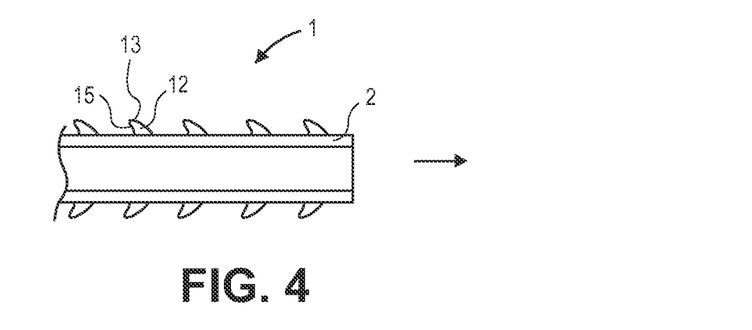
FIG. 4 illustrates a cross-sectional view of a delivery catheter in accordance with an embodiment of the present invention.

In accordance with some embodiments of the present invention, improvements may be made to a delivery catheter to induce trauma and create faster tubal occlusion. Tissue trauma may be generated by features of the delivery catheter in order to create a greater tissue healing response. In an embodiment illustrated in FIG. 4, the outer surface of elongated shaft 2 of delivery catheter 1 is provided with a shark skin, or oriented textures 12 near a distal end of elongated shaft 2. As illustrated in FIG. 4, the shark skin, or oriented texture 12 has the appearance of a first dorsal fin having a triangular shape. In an embodiment, leading edge 13 and trailing edge 15 of the oriented texture 12 are flat. In another embodiment, leading edge 13 and trailing edge 15 may have a curved, streamlined shape. The texture 12 allows for smooth entry into a fallopian tube in the direction of the arrow, whereas retraction of the delivery catheter in the opposite direction results in trauma to the inside of the tube.

In an embodiment, a delivery catheter comprising elongated shaft 2 of FIG. 4 is advanced within a fallopian tube with the leading distal end of the elongated shaft being advanced to or beyond the projected delivery site of the occlusion device. The delivery catheter is then retracted creating trauma at the projected delivery site, and the occlusion device is expelled at the projected delivery site. The trauma created during retraction of the delivery catheter may promote the healing response and tissue in-growth into the deposited occlusion device, resulting in faster tubal occlusion.

Figure 5A:
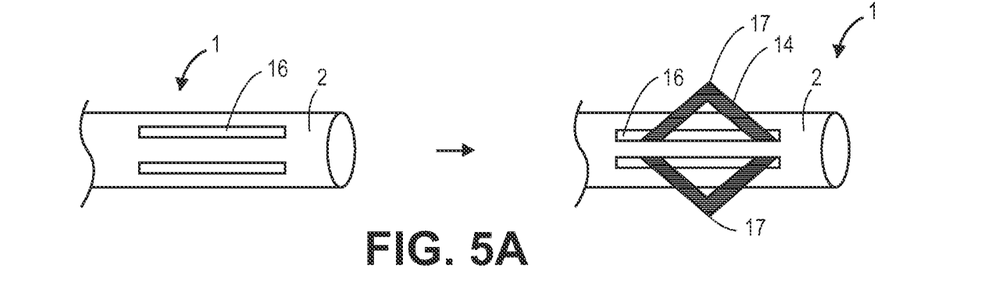
FIG. 5A illustrates a side view of a delivery catheter in accordance with an embodiment of the present invention.
Figure 5B:
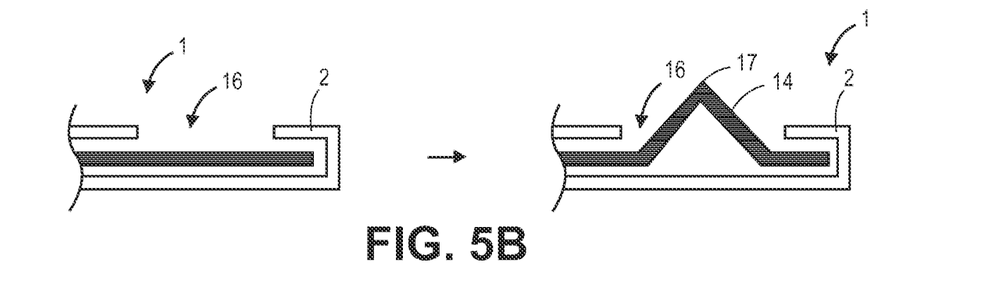
FIG. 5B illustrates a cross-sectional view of a delivery catheter of FIG. 5A in accordance with an embodiment of the present invention.

In an embodiment illustrated in FIG. 5A and FIG. 5B an elongated shaft 2 of delivery catheter 1 may be equipped with one or more features that may expand to cause trauma and retract back into the elongated shaft 2 prior to or during withdrawal of the delivery catheter from the patient. In an embodiment, features are wires 14 that expand through slits 16 in a distal end portion of elongated shaft 2. Wires 14 can be expanded, for example by pushing the wires 14 forward distally in elongated shaft 2, to induce trauma before or while the occlusion device is deployed, and retracted, for example by withdrawing the wires 14 proximally in elongated shaft 2, prior removing the delivery catheter 1 from the fallopian tube to avoid trauma to the ostium. In an embodiment, the wires 14 can be expanded to form an apex 17 to induce trauma.

Figure 6:
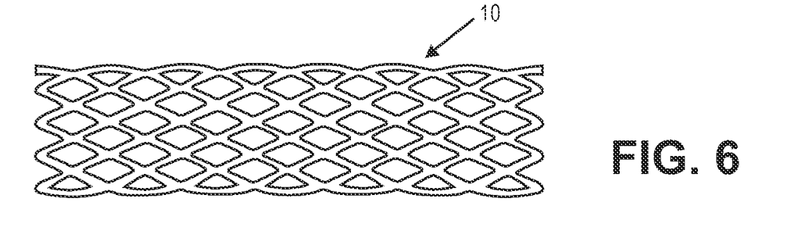
Figure 7:
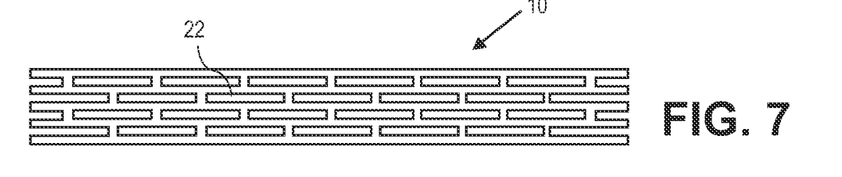

The delivery catheters 1 in accordance with embodiments of the invention can be used to deliver a variety of occlusion devices such as, but not limited to those illustrated in FIGS. 6-19C. For example, FIGS. 6-7 illustrate a tubular self-expanding occlusion device 10 which comprises a length of metal tubing such as a shape memory nitinol having slots 22. The occlusion device 10 may conform to a relatively small dimensioned configuration for introduction and advancement into the patient's body lumen as illustrated in FIG. 7, and expand to a larger, open configuration when deployed within a body lumen as illustrated in FIG. 6. The slots 22 cut into the wall of the tubing allow self-expansion of the occlusion device 10 into the open configuration of FIG. 6.

Figure 8:
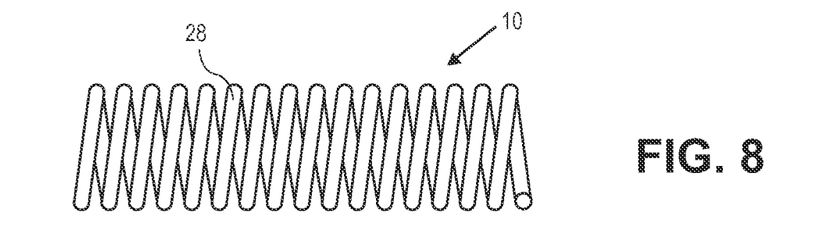
Figure 9:
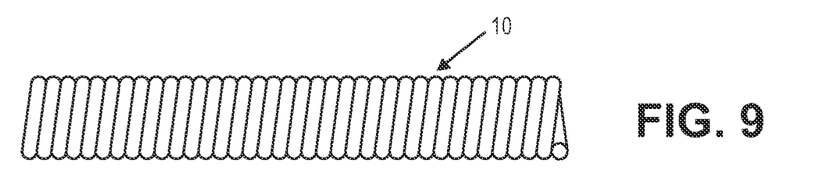

FIG. 8 and FIG. 9 illustrate an occlusion device 10 including a coil 28 of shape memory wire or ribbon, such as nitinol. The coil 28 may conform to a relatively small dimensioned configuration for introduction and advancement into the patient's body lumen as illustrated in FIG. 9 and expand to a larger, open configuration when deployed within a body lumen as illustrated in FIG. 8.

Figure 10A:
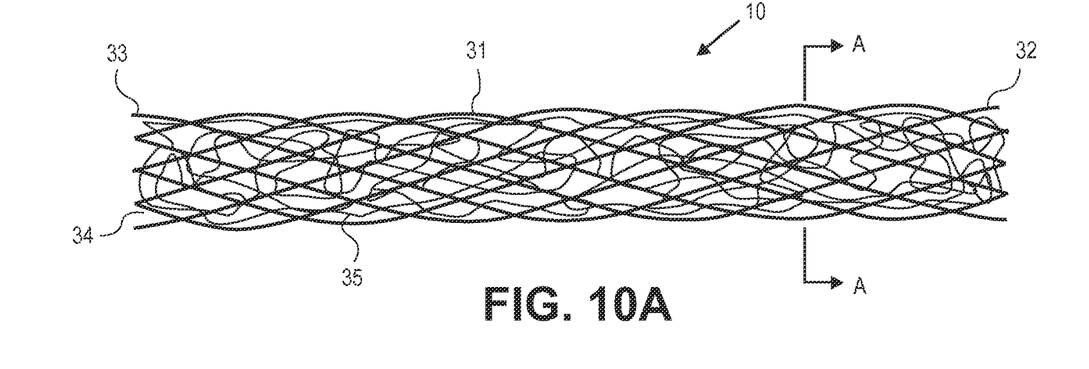
Figure 10B:
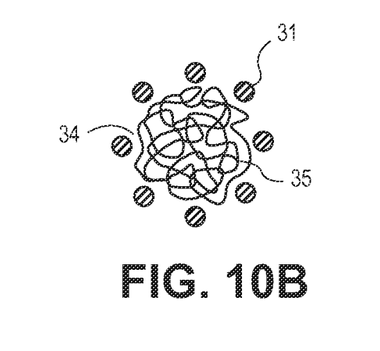
FIG. 10B illustrates a cross-sectional view taken along line A-A of the occlusion device illustrated in FIG. 10A in accordance with embodiments of the present invention.

FIG. 10A an 10B illustrate an occlusion device 10 generally comprising a tubular member 31 with an open framework, which may be restrained in a relatively small dimensioned configuration for the introduction and advancement into the patient's body and self-expand into a larger, open configuration when deployed as illustrated in FIG. 10A and FIG. 10B. Occlusion device 10 has a first end 32, a second end 33 and a lumen 34 extending therein. As shown in FIG. 10B illustrating a transverse cross section of the tubular member 31 shown in FIG. 10A, taken along lines A-A, a tissue in-growth member 35 may be transversely disposed on, within or entangled with tubular member 31.

Tissue in-growth member 35 may be permeable to allow for tissue in-growth. The permeability of the tissue in-growth member 35 facilitates epithelialization, and the epithelialized tissue in-growth may permanently occlude the reproductive body lumen sufficiently to prevent the passage of reproductive cells therethrough. In an embodiment, tissue in-growth member 35 comprises fibers, which may be bundled or woven strands, or a mesh of bundles or woven strands. In an embodiment, member 35 may comprise a sheet of woven material disposed on tubular member 31 or in the lumen 34 of tubular member 31. A variety of materials may be used to form the tissue in-growth member 35, including plastics, polymers, metals, and treated animal tissues. For example, in-growth member 35 may include polyethylene terephthalate (PET) or silk fibers. In an embodiment, tissue in-growth member 35 is an irritant, such as PET or Nylon, which promotes epithelialization. Additionally, tissue in-growth member 35 may be coated or otherwise impregnated with cell growth stimulators, hormones, and/or chemicals to enhance tissue impregnation.

While tissue in-growth member 35 is illustrated and described specifically with regard to FIG. 10A and FIG. 10B, it is understood that tissue in-growth member 35 can be utilized with other embodiments of the invention, including the occlusion devices illustrated in the remainder of FIG. 6-FIG. 19C. Accordingly, while tissue in-growth member 35 may not be illustrated or described for each of FIG. 6-FIG. 19C, it is understood that this omission has been made in order to more clearly illustrate and not obscure other aspects in accordance with embodiments of the present invention.

Figure 11A:
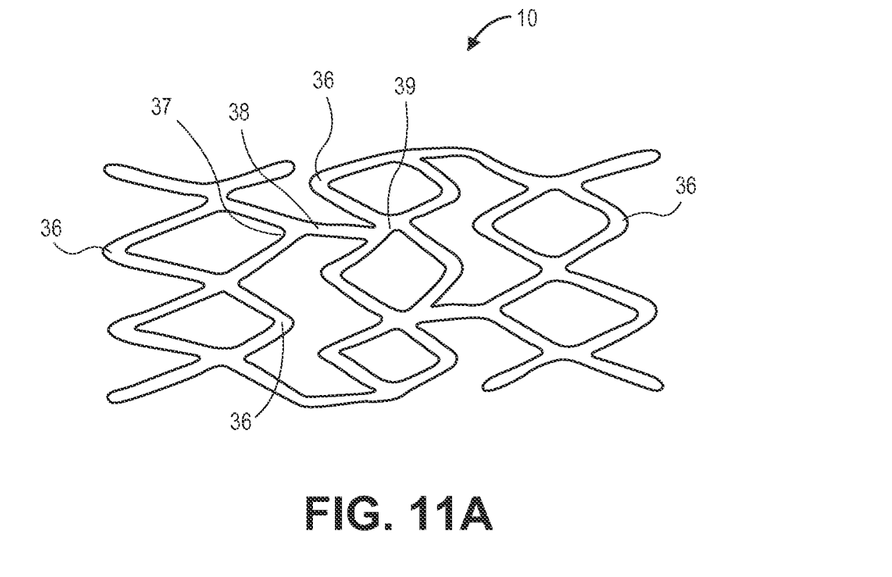
FIG. 11A illustrates a side view of an occlusion device in accordance with an embodiment of the present invention.
Figure 11B:
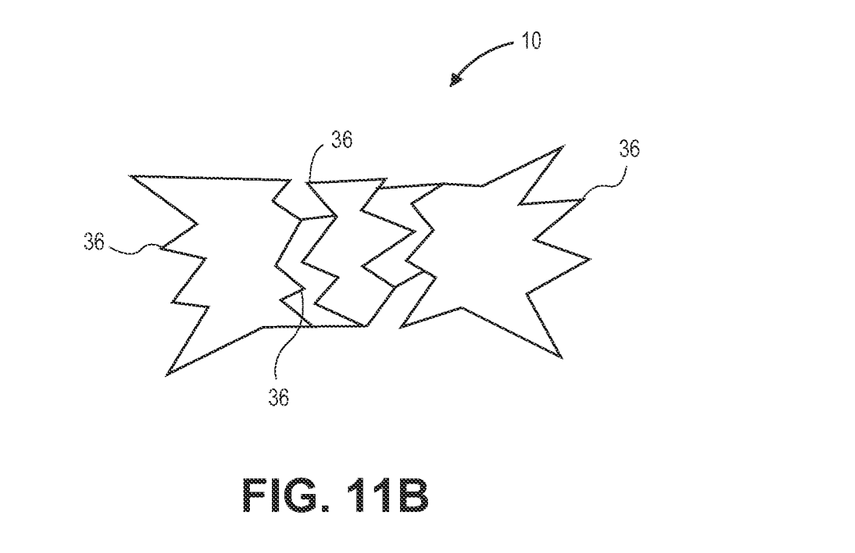
FIG. 11B illustrates a top view of FIG. 11A in accordance with an embodiment of the present invention.

In accordance with some embodiments of the present invention, improvements may be made to an occlusion device to prevent migration and induce trauma. In an embodiment illustrated in FIG. 11A-11B, occlusion device 10 comprises an expandable frame that has features to both engage a body lumen to prevent migration and induce trauma within the body lumen. As shown, the occlusion device 10 has an open framework comprising triangular or diamond-like shapes. Occlusion device 10 may have a general tubular shape, with the closed ends 36 of the triangular or diamond-like shapes facing outward from the occlusion device 10 in radial, proximal and distal directions in a starburst-like configuration to create engagement anchors, which may function to prevent migration and induce trauma within a body lumen, such as a fallopian tube. As provided in the side view illustration of FIG. 11A, occlusion device 10 may be characterized by rows of stacked diamond-like shapes, with the adjacent rows being connected with traverse members 38. Traverse member 38 connects a side end 37 of a diamond-like shape opposite the closed end 36 to a top/bottom end 39 of a diamond-like shape. As illustrated, traverse members 38 may be periodically disposed. A period of every other diamond-like shape is illustrated in FIG. 11A-11B, though embodiments include other periods of one or greater.

Occlusion device 10 may further be provided with a tissue in-growth member similar to that in FIG. 10A and FIG. 10B. For example, occlusion device may be entangled with PET or silk fibers to cause a tissue response. Occlusion device 10 may further be provided with a membrane attached similar to the membrane illustrated in FIG. 12D to the outer surfaces to create and instantaneous occlusion.

Figure 12A:
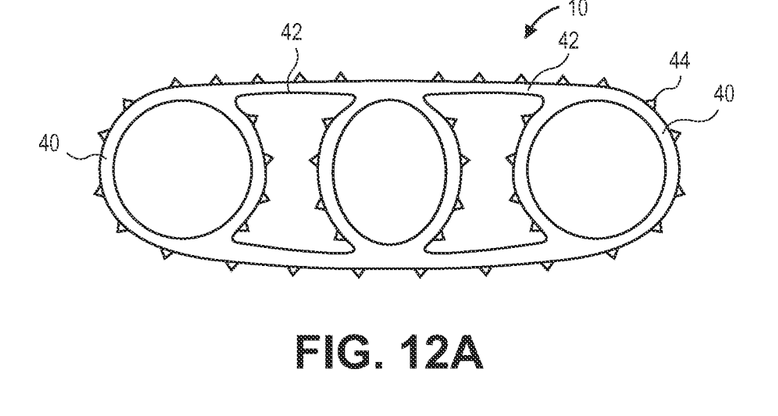
FIG. 12A illustrates a top view of an occlusion device in accordance with an embodiment of the present invention.
Figure 12B:
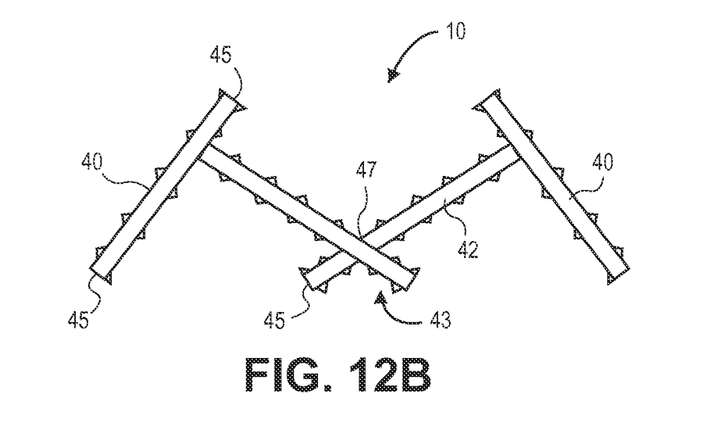
FIG. 12B illustrates a side view of FIG. 12A in accordance with an embodiment of the present invention.
Figure 12C:
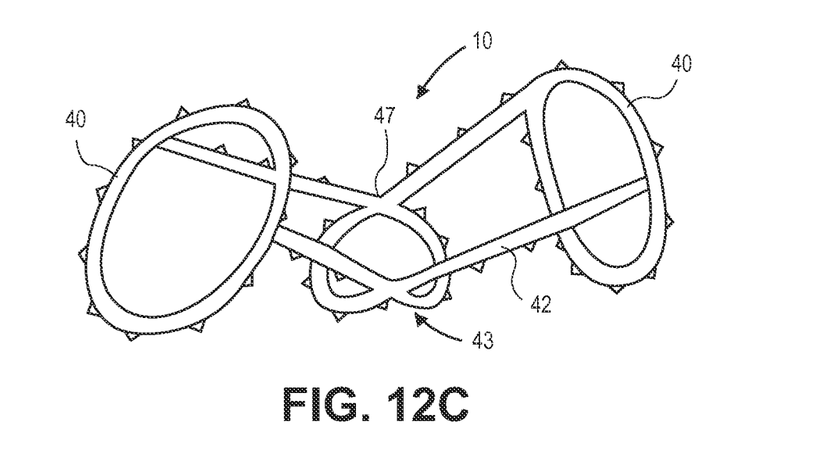
FIG. 12C illustrates an isometric view of FIG. 12A in accordance with an embodiment of the present invention.

In an embodiment illustrated in FIGS. 12A-12E, occlusion device 10 comprises a series of linked ovals. FIG. 12A illustrates a top view of the occlusion device in a flat configuration, where FIGS. 12B and 12C illustrate side and isometric views, respectively, of the occlusion device in an expanded configuration. In an embodiment, occlusion device 10 may be restrained in a flat or rolled-up configuration for the introduction and advancement into the patient's body and expand into a larger, open configuration when deployed as illustrated FIG. 12B-FIG. 12D. Ovals 40 may be connected by U-shaped traverse members 42 which are also connected at joints 47. When in the expanded configuration, connected U-shaped traverse members 42 form a folded oval shape 43 as illustrated in FIGS. 12B-12C.

Ovals 40 at the proximal and distal ends of the occluding member are not folded. Trauma inducing features 44 may additionally be provided on the occlusion device 10, such that when in the expanded configuration ends 45 may engage the tube to prevent migration and induce trauma within the tube.

Figure 12D:
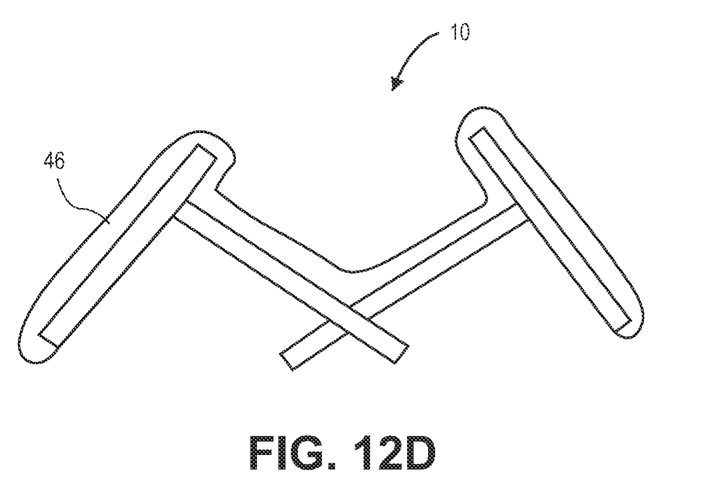
FIG. 12D illustrates a side view of an occlusion device in accordance with an embodiment of the present invention.
Figure 12E:
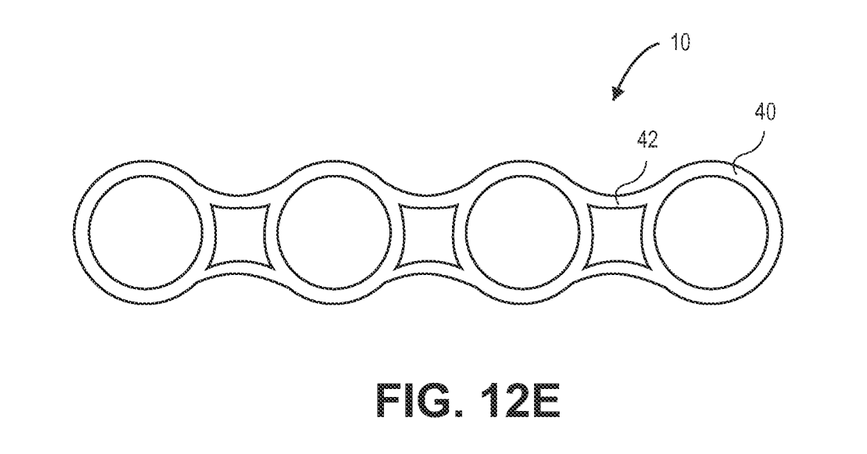
FIG. 12E illustrates a top view of an occlusion device in accordance with an embodiment of the present invention.

In an embodiment illustrated in FIG. 12D a membrane 46 may be formed on the occlusion device 10 to create a physical barrier to material transfer within the tube. Membrane 46 can be a variety of materials such as, but not limited to, a polymeric sheet, closed cell foam or fabric and may be composed of a variety of layers to create an impermeable surface or a surface that promotes tissue in-growth. In an embodiment, the membrane provides an immediate blockade to material transfer within the tube, providing benefits to the patient prior to the completion of the healing and tissue in-growth process. FIG. 12E is an illustration of an alternative occlusion device, with additional ovals 40 and traverse members 42.

Figure 13A:
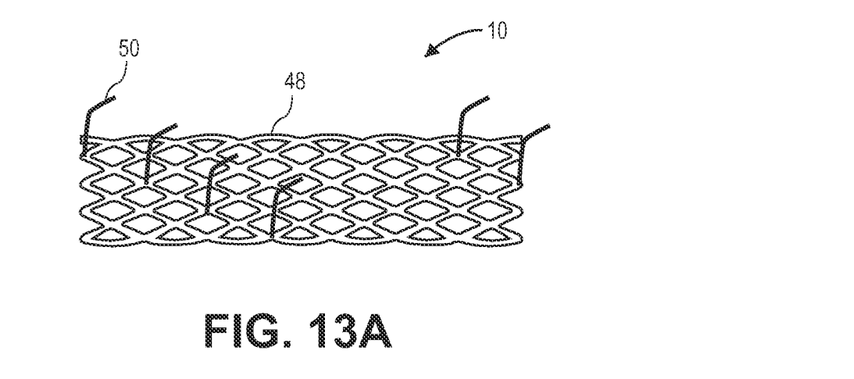
FIG. 13A illustrates a side view of an occlusion device in accordance with an embodiment of the present invention.
Figure 13B:
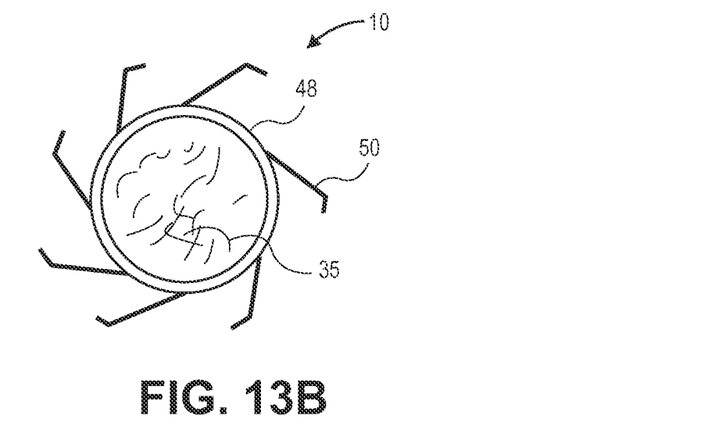
FIG. 13B illustrates a cross-sectional view of FIG. 13A in accordance with an embodiment of the present invention.
Figure 13C:
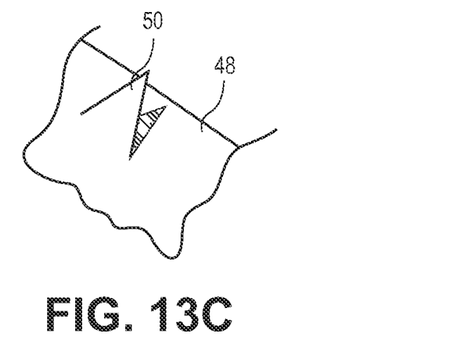
FIG. 13C-FIG. 13D illustrate isometric views of FIG. 13A in accordance with embodiments of the present invention.
Figure 13D:
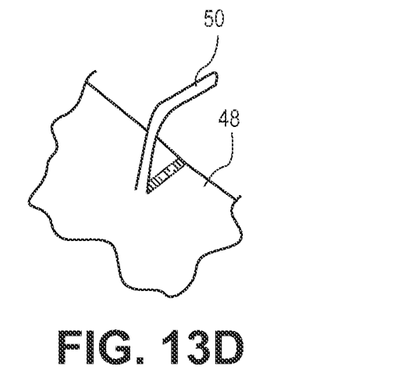

FIGS. 13A-13D illustrate an embodiment which may both engage the tube to prevent migration and induce trauma within the tube. Occlusion device 10 may include a tubular self-expanding nitinol frame 48 with protruding features 50 in a helical arrangement to engage the tubal tissue. The occlusion device 10 may conform to a relatively small dimensioned configuration for introduction and advancement into the patient's body lumen, and expand to a larger, open configuration when deployed within the tube. In an embodiment, the only features 50 protruding from the surface of the frame 48 are those which are arranged in a helical arrangement. For example, the protruding features 50 can be formed in the shape of triangles as illustrated in FIG. 13C, or as wire-like prongs as illustrated in FIG. 13D. The helical formation of the plurality of protruding features 50 allows the frame 48 to engage the tubal tissue and maintain the position of the occlusion member 10. It is thought that the particular helical formation of protruding features 50 torques the occlusion device into the fallopian tube thereby resisting displacement by the natural peristaltic pumping forces. The protruding features 50 also generate a tissue healing response by causing trauma. Occlusion device 10 may further be provided with a tissue in-growth member 35 similar to that in FIG. 10A and FIG. 10B. For example, occlusion device may be entangled with PET, silk or Nylon fibers.

Figure 14A:
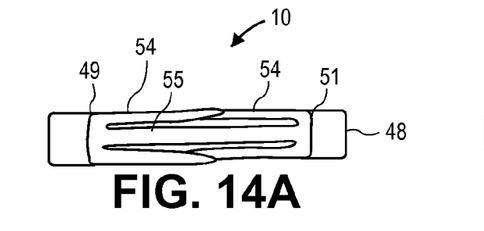

FIG. 14A-17B illustrate embodiments in which the occlusion device may comprise arms which may expand outward from the occlusion device in opposing directions to prevent migration and induce trauma. Occlusion device 10 may be comprised of a nitinol frame 48 that is contoured and formed to be compressed into a tube shape as illustrated in FIG. 14A, and expand such that the central arms 54 expand outward in opposing directions offering fixation and tissue trauma means. Central arms 54 may be self-expandable or may be expandable by deflection. Occlusion device 10 may include a proximal portion 49, a distal portion 51, and a traverse member SS connecting said proximal portion 49 and said distal portion 51. A first plurality of arms 54 are outwardly expandable from the proximal portion 49, and a second plurality of arms are outwardly expandable from the distal portion 51 in an opposing direction to the first plurality of arms. The first plurality of arms and second plurality of arms may face opposing directions and overlap in both the expanded and restrained/compressed configurations.

Figure 14B:
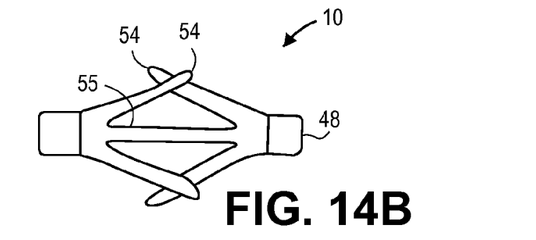
Figure 15A:
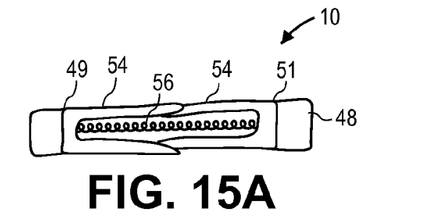
Figure 15B:
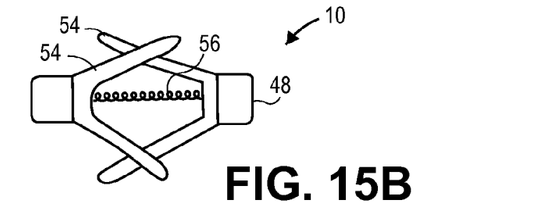

In the embodiment illustrated in FIGS. 14A-14B, the proximal and distal portions of the occlusion member 10 are separated by rigid traverse member 55 located long a central axis of the occlusion device, and the overall length of the occlusion device 10 remains the same when in the restrained/compressed and expanded states. In such an embodiment, the arms 54 may self-expand when in an unrestrained state. In an embodiment illustrated in FIG. 15A-15B, the proximal and distal ends of the occlusion device 10 are separated by a contractible traverse member 56, such as a spring. In an embodiment, the contractible traverse member 56 is stretched when in a restrained/compressed position inside the delivery catheter as illustrated in FIG. 15A. Upon delivery, the arms 54 of occlusion device 10 are allowed to expand and the contractible traverse member 56 is allowed to contract. The contracting traverse member 56 may additionally force the arms 54 outward as they are deflected away from opposing arms 54 or other portions of the occlusion device 10. In an embodiment, the plurality of arms 54 are deflected radially outward from contractible transverse member 56, such as a spring, located along a central axis of the occlusion device 10. Arms 54 may also self-expand when unrestrained. Occlusion device 10 may further be provided with a tissue in-growth member 35 similar to that in FIG. 10A and FIG. 10B. For example, occlusion device may be entangled with PET, silk or Nylon fibers.

Figures 16A, 16B:
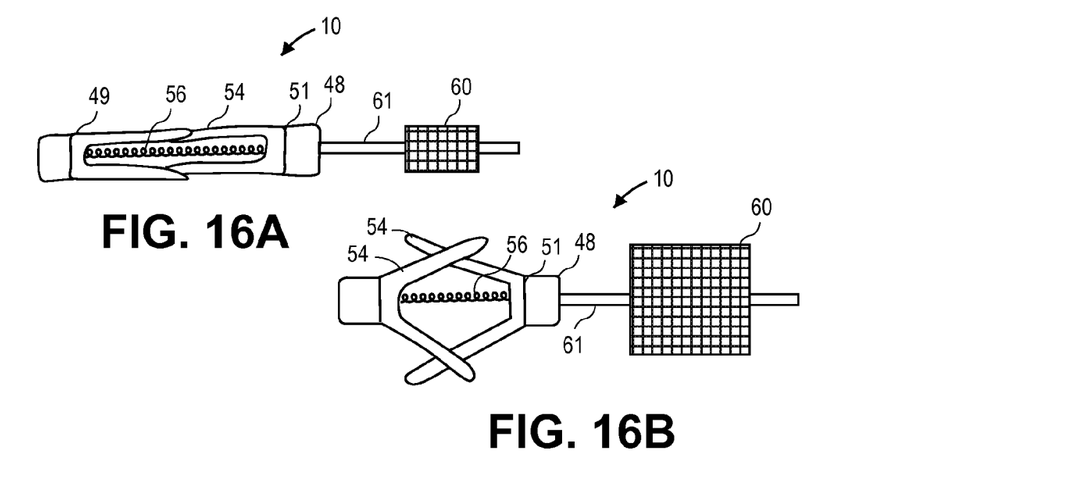

FIG. 16A-16B illustrate an embodiment in which occlusion device 10 may comprise radially expandable arms 54, spring 56 and an expandable plug 60. FIG. 16A illustrates the plug 60 in an unexpanded state, such as when in the delivery catheter. After deployment within a body lumen, the plug 60 absorbs body fluid and radially expands to an expanded state as illustrated in FIG. 16B. The plug 60 can be formed from a variety of materials such hydrogel polymers, open celled foams, etc. The addition of plug 60 allows for immediate occlusion of the body lumen. In an embodiment, plug 60 may be a cylindrical sleeve positioned over a tubular extension 61 extending from said distal portion 51 along the central axis of the occlusion device 10.

Figure 17A:
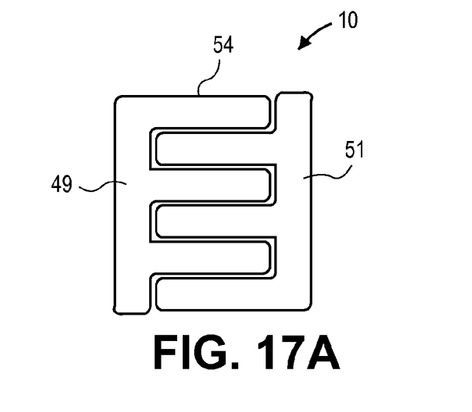
Figure 17B:
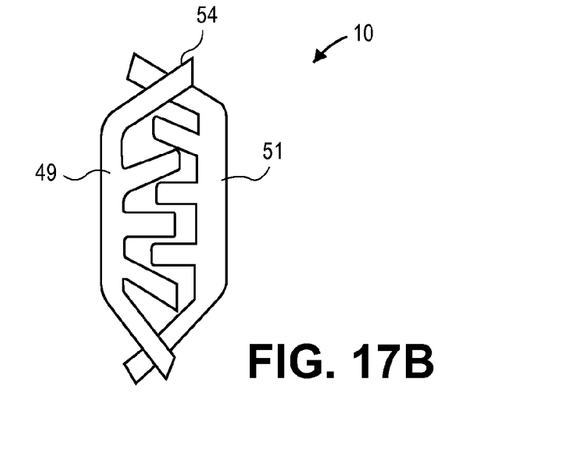

FIG. 17A-17B illustrate an embodiment including interlocking arms 54. In an embodiment, the proximal and distal portions 49, 51 of the occlusion device 10 are brought toward each other when the device is unconstrained, causing the interlocking arms 54 to expand outward from the frame in opposing directions to create an interlocking network of struts or barbs to engage the tube. The ends of the arms 54 are pushed together, thereby deflecting the arms 54 outward. The proximal end portion 49 and distal end portion 51 may be connected with a contractible traverse frame member 56, such as described with regard to FIG. 15A-FIG. 15B.

Figure 18A:
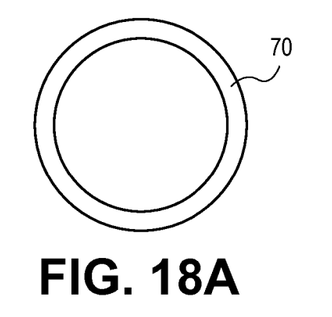
FIG. 18A-FIG. 18B illustrate cross-sectional views of occlusion devices in accordance with embodiments of the present invention.
Figure 18B:
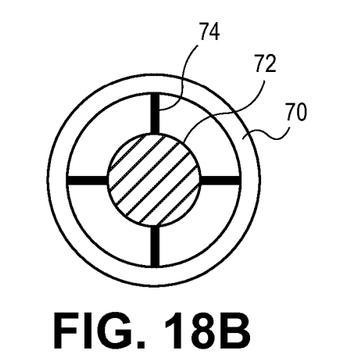
Figure 18C:
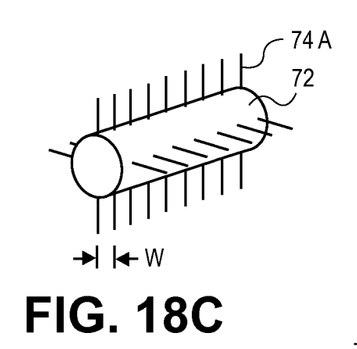
FIG. 18C-FIG. 18E illustrate isometric views of occlusion devices in accordance with embodiments of the present invention.
Figure 18D:
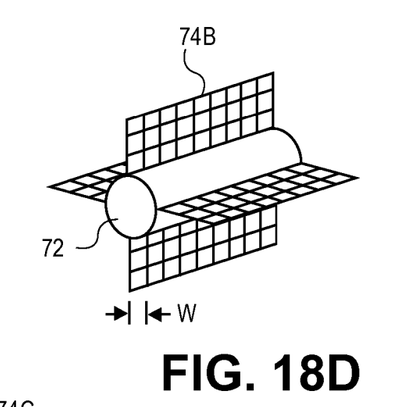
Figure 18E:
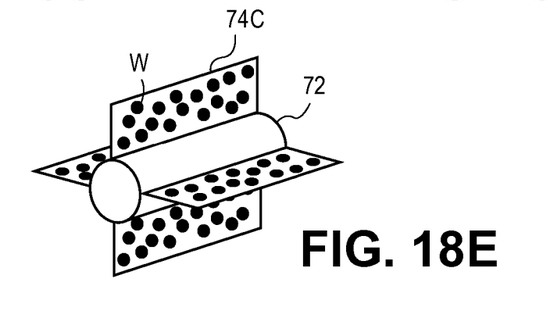

FIGS. 18A-19C illustrate embodiments in which the total volume of in-growth required to occlude a body lumen may be reduced compared to conventional expansive occluding devices. An expandable tubular frame member 70 is illustrated in FIG. 18A. As illustrated in FIG. 18B a polymer or metallic rod 72 is disposed within and running through the center of the tubular frame 70. In an embodiment, rod 72 is substantially solid. In an embodiment, rod 72 is impermeable. A surface of the rod 72 may be scored to promote tissue in-growth. Lines of tissue in-growth material 74 may also be formed on the surface of the rod 72. Tissue in-growth material 74 can be, but is not limited to, a series of fibers 74A as illustrated in FIG. 18C, a mesh 74B as illustrated in FIG. 18D, and a porous materials 74C as illustrated in FIG. 18E. In an embodiment, the width between fibers 74A, pores in the mesh 74B, or pore size in the porous material 74C have a width W between 200 and 600 microns. The rod 72 functions to fill the internal volume of the frame member 70, thereby reducing the distance that the in-growth must travel before completely filling all the empty space within the frame member 70. In an embodiment, rod 72 fills at least half of the cross-sectional area of the frame 70 as illustrated in FIG. 18B.

Figure 19A:
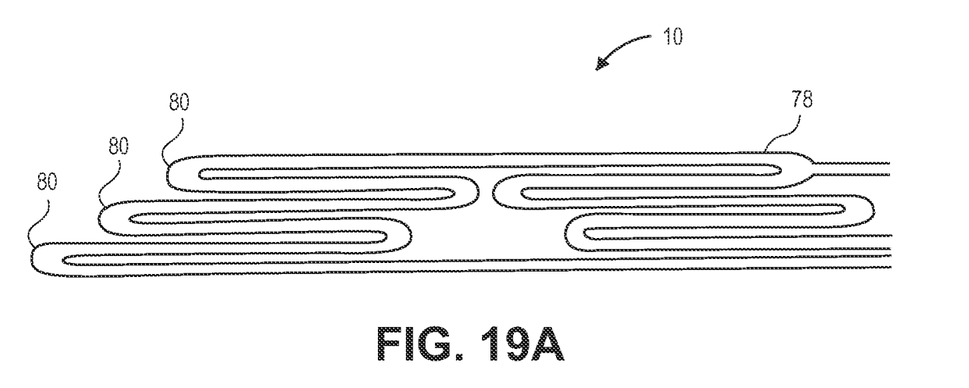
FIG. 19A illustrates a top view of an occlusion device in accordance with an embodiment of the present invention.

FIG. 19A is an illustration of an occlusion device 10 which may be deliverable into body lumen in a substantially oblong or flat geometry. By stretching the fallopian tube in one direction, the opposing sides of the tube may be brought into closer proximity to one another. Therefore, tissue growing into the occlusion device may not need to travel as far as it would if the occlusion device were circular in cross section, and may result in less time to total occlusion of the fallopian tube.

Figure 19B:
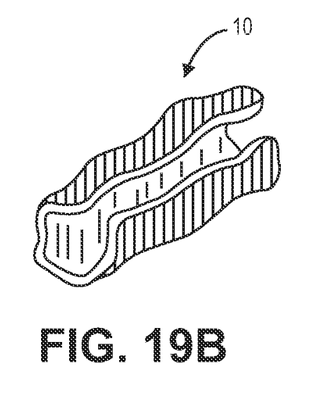
FIG. 19B-FIG. 19C illustrate isometric views of occlusion devices in accordance with embodiments of the present invention.
Figure 19C:
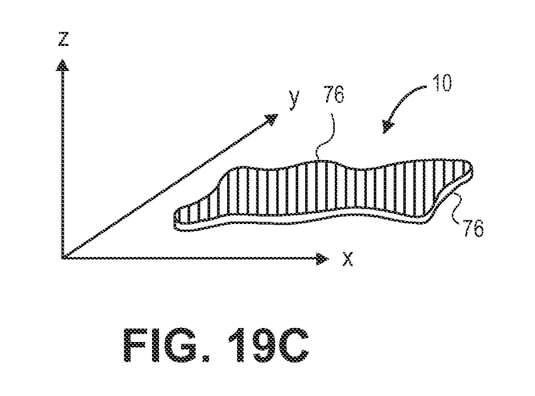

In an embodiment, the occlusion device 10 has a substantially flat geometry when unconstrained. Occlusion device 10 may be delivered in a catheter in a rolled-up configuration as illustrated in FIG. 19B. Once expelled from the delivery catheter, occlusion device 10 spreads out in a plane and forms a substantially flat geometry in the tube, as illustrated in FIG. 19C. In an embodiment, the planar edges 76 of the occlusion device can be formed with a wavy profile, which may assist in allowing the occlusion device 10 to fully spread out in a substantially planar, flat configuration.

Referring again to FIG. 19A, occlusion device 10 may be formed of an open walled frame 78. Open walled frame 78 may have a closed loop path to avoid any having any sharp edges encumber the spreading out of the device 10 within the tube. In an embodiment, frame 78 is characterized by a path having staggered levels of cutbacks 80. In an embodiment, frame 78 comprises at least three staggered levels of cutbacks 80. In an embodiment, occlusion device 10 may be cut from a flat nitinol sheet. In another embodiment, occlusion device 10 may be a conventional tubular occlusion device which has been flattened into a planar configuration. Occlusion device 10 may further be provided with a tissue in-growth member similar to that in FIG. 10A and FIG. 10B. For example, occlusion device may be entangled with PET, silk or Nylon fibers. In an embodiment the frame is constrained within the catheter in a rolled up tubular configuration, and when expelled from the cateter opposite side edges of the frame spread out in a plane and the frame assumes a substantially flat configuration entirely across x-y dimensions in the plane. The opposite side edges of the frame may run along an axial length of the catheter when the frame is in the rolled up tubular configuration. When in the rolled up tubular configuration the frame may be characterized by a transverse cross section width, and when in the substantially flat configuration the frame may be characterized by a transverse width between the opposite side edges that is greater than the transverse cross section width.

In the foregoing specification, various embodiments of the invention have been described. It will, however, be evident that various modifications and changes may be made thereto without departing from the broader spirit and scope of the invention as set forth in the appended claims. The specification and drawings are, accordingly, to be regarded in an illustrative sense rather than a restrictive sense. Hence, the scope of the present invention is limited solely by the following claims.

What is claimed is:

1. A fallopian tube occlusion system comprising:
a catheter that is sized and shaped to be inserted through a cervix, into a uterus, and guided into a fallopian tube through a tubal ostium; and
an occlusion device including an open walled frame that forms a closed loop path and is characterized by levels of cutbacks with substantially rounded edges, wherein a width of the occlusion device progressively widens down the levels of the cutbacks:
wherein the frame is constrained within the catheter in a rolled up tubular configuration, and when expelled from the catheter within the fallopian tube opposite side edges of the frame spread out in a plane and the frame assumes a substantially flat configuration within the fallopian tube entirely across x-y dimensions in the plane such that the frame stretches the fallopian tube in one direction, and opposite sides of the fallopian tube are brought into closer proximity to one another;
wherein opposite side edges of the frame expand from the rolled up tubular configuration to the substantially flat configuration to have a wavy profile.

2. The fallopian tube occlusion system of claim 1, wherein the opposite side edges are wavy edges designed to engage a tubal wall of the fallopian tube.

3. The fallopian tube occlusion system of claim 2, further comprising a tissue in-growth material.

4. The fallopian tube occlusion system of claim 1, wherein the opposite side edges of the frame expand after being expelled from the catheter.

5. The fallopian tube occlusion system of claim 1, further comprising a tissue in-growth member that includes at least one of polyethylene terephthalate (PET), silk, and nylon fibers.

6. The fallopian tube occlusion system of claim 1, wherein said open walled frame comprises at least three staggered levels of cutbacks.

7. The fallopian tube occlusion system of claim 1, wherein the opposite side edges of the frame run along an axial length of the catheter when the frame is in the rolled up tubular configuration.

8. The fallopian tube occlusion system of claim 1, wherein the rolled up tubular configuration of the frame is characterized by a transverse cross section width, and the substantially flat configuration is characterized by a transverse width between the opposite side edges that is greater than the transverse cross section width.

* * * * *